(12) United States Patent
Luciano et al.

(10) Patent No.: US 11,903,836 B2
(45) Date of Patent: Feb. 20, 2024

(54) ANTHROPOMETRIC POSTERIOR CONDYLE

(71) Applicant: Howmedica Osteonics Corp., Mahwah, NJ (US)

(72) Inventors: Camila Luciano, Chicago, IL (US); Kenneth Pascale, Hoboken, NJ (US); James V. Bono, Dover, MA (US); Olivia Jane Bono, Dover, MA (US)

(73) Assignee: Howmedica Osteonics Corp., Mahwah, NJ (US)

( * ) Notice: Subject to any disclaimer, the term of this patent is extended or adjusted under 35 U.S.C. 154(b) by 187 days.

(21) Appl. No.: 17/508,211

(22) Filed: Oct. 22, 2021

(65) Prior Publication Data

US 2022/0125592 A1  Apr. 28, 2022

Related U.S. Application Data

(60) Provisional application No. 63/106,385, filed on Oct. 28, 2020.

(51) Int. Cl.
  *A61F 2/38* (2006.01)
(52) U.S. Cl.
  CPC .......... *A61F 2/3859* (2013.01); *A61F 2/3886* (2013.01)
(58) Field of Classification Search
  None
  See application file for complete search history.

(56) References Cited

U.S. PATENT DOCUMENTS

| 7,584,080 B2 | 9/2009 | Taylor et al. |
| 9,861,489 B2 | 1/2018 | Siebel |
| 2008/0009950 A1 | 1/2008 | Richardson |
| 2008/0140212 A1* | 6/2008 | Metzger ............... A61F 2/3886 623/20.14 |
| 2010/0249940 A1* | 9/2010 | Sanford ................. A61F 2/389 623/20.27 |
| 2011/0194739 A1 | 8/2011 | Vincent et al. |
| 2015/0257889 A1 | 9/2015 | Kang |
| 2022/0265432 A1* | 8/2022 | Sadile .................. A61F 2/3859 |

OTHER PUBLICATIONS

Ehmke, et al., Anthropometric Measures of the Posterior Condyles: Gender Differences and Correlation to Implant Sizing, The Journal of Knee Surgery, 2019, 6 pages, vol. 00, No. 0.
Hitt, et al., Anthropometric Measurements of the Human Knee: Correlation to the Sizing of Current Knee Arthroplasty Systems, The Journal of Bone and Joint Surgery, 2003, pp. 115-122, vol. 85-A, Supplement 4.

* cited by examiner

*Primary Examiner* — Jerrah Edwards
*Assistant Examiner* — Jacob Lee Fincher
(74) *Attorney, Agent, or Firm* — Lerner David LLP

(57) ABSTRACT

A femoral component for a prosthesis used in a total knee arthroplasty includes a posterolateral taper on the lateral condyle. The lateral and medial condyles of the femoral component are asymmetric to accommodate for the asymmetry of a resected lateral and medial condyle of a femur. The taper is designed to improve the fit of femoral component on the femur to eliminate or reduce overhang of the femoral component's lateral condyle, thereby reducing pain, irritation, stiffness, soreness, or any other symptoms of an improperly fitting prosthesis.

20 Claims, 5 Drawing Sheets

ANTHROPOMETRIC POSTERIOR CONDYLE

CROSS-REFERENCE TO RELATED APPLICATIONS

This application claims the benefit of the filing date of U.S. Provisional Application No. 63/106,385 filed Oct. 28, 2020, the disclosure of which is hereby incorporated by reference herein in its entirety.

BACKGROUND OF THE INVENTION

Patients who undergo a total knee arthroplasty (TKA) may have a portion of the femur resected in preparation for receiving a prosthesis. Surgeons who employ conventional surgical techniques may observe asymmetry of the medial and lateral femoral condyles. Clinical data show the femoral posterior condyles are asymmetric in width, with the lateral side being smaller than the medial side. That is, the lateral condyle is typically smaller in width than the medial condyle. However, this is not sufficiently accounted for in currently available femoral components, which presume greater symmetry between the condyles, often resulting in the femoral component being larger than the bone it is in contact with. Such mismatch often creates a posterolateral overhang of the femoral component on the posterolateral femoral condyle (i.e., the smaller of the condyles) on a lateral side of the lateral condyle and/or a medial side of the lateral condyle facing the intercondylar notch. Such overhang may produce symptomatic impingement of the surrounding capsular tissue and altered ligament tensioning. This can lead to soft tissue irritation, stiffness and further surgical intervention to restore range of motion, such as manipulation under anesthesia or a revision TKA. Patients who undergo revision TKA for stiffness, historically have worse outcomes then those who did not. In addition to correctly balancing the knee, properly fitting components are important to achieving the elimination of symptomatic knee pain, restoration of range of motion, and avoiding a revision procedure. Such patients would benefit from newer component design which accounts for this asymmetry.

While studies have shown that the posterolateral femoral component area does not symmetrically match the size of the posteromedial femoral component area, the ratio of the size difference between the two areas is nearly identical between males and females. Thus, a universal change to the current design to a more conforming design that may accommodate the asymmetry of the condylar sizes to avoid symptomatic overhang is therefore desired.

BRIEF SUMMARY OF THE INVENTION

The present disclosure describes a femoral component for use as part of a prosthesis for a total knee arthroplasty (TKA). The femoral component includes a taper on the component's posterolateral condyle to accommodate for the varying sizes of a resected medial and lateral femoral condyle. The taper may improve the fit of the prosthesis by reducing or eliminating overhang of the femoral component on the lateral side of the condyle or on the side of the intercondylar notch. Improved fit of the femoral component may relieve a patient of potential pain, irritation, stiffness, reduced range of motion, and the like caused by the implant, and also may prevent or delay the need for a TKA revision surgery.

In certain embodiments, a femoral component for a knee prosthesis may include an anterior flange. The femoral component may further include a medial condyle extending from the anterior flange to a posterior end thereof and having inner and outer edges defining a medial condyle width therebetween, the inner edge lying substantially along a single plane from the anterior flange to the posterior end of the medial condyle. The femoral component may further include a lateral condyle extending from the anterior flange to a posterior end thereof and having inner and outer edges defining a lateral condyle width therebetween, the inner edge of the lateral condyle having a first portion, a second portion, and an intermediate portion. The inner edges of the lateral and medial condyles may define an intercondylar notch and lateral and medial extents of the intercondylar notch such that an intercondylar width extends between the inner edges of the lateral and medial condyles. The inner edge of the lateral condyle tapers toward the outer edge of the lateral condyle at the intermediate portion such that the width of the intercondylar notch is greater along the second portion of the inner edge of the lateral condyle than along the first portion of the lateral condyle.

The intermediate portion of the inner edge of the lateral condyle may begin at 70-75% of an anteroposterior length of the femoral component from an anterior extent of the femoral component. The femoral component may include a bone contacting side having a plurality of planar bone contacting surfaces comprised of an anterior surface, a distal surface, a posterior surface, an anterior chamfer surface, and a posterior chamfer surface, the anterior chamfer surface being disposed between the anterior surface and distal surface, the posterior chamfer surface being disposed between the distal surface and posterior surface. The intermediate portion of the inner edge of the lateral condyle may be intersected by the posterior chamfer surface. The intermediate portion may have a length extending in an anteroposterior direction that is no longer than a length of the posterior chamfer surface. The intermediate portion may have an anteroposterior length of 10% to 15% the full anteroposterior length of the femoral component. The first portion of the inner edge may lie in a first plane and the second portion of the inner edge may lie in a second plane. The second plane may be offset and parallel to the first plane. The second portion may extend from the intermediate portion to the posterior end of the lateral condyle. The width of the intercondylar notch may be constant along the first portion of the inner edge of the lateral condyle. The anterior flange may define an anterior extent of the intercondylar notch, the anterior extent of the intercondylar notch being arc shaped. The lateral condyle may have a condylar width defined between the inner and outer edges thereof, the condylar width tapering from wider to narrower in a posterior direction along the inner edge of the intermediate portion such that the condylar width is narrower at the second portion of the inner edge than at the first portion of the inner edge.

The intercondylar notch may be asymmetric. The lateral condyle may have a condylar width along a length of the second portion that is up to 20% less than the condylar width of the medial condyle at the same length of the medial condyle. The intermediate portion of the inner edge of the lateral condyle may extend linearly toward the posterior end of the femoral component and the outer edge of the lateral condyle. The inner edge of the lateral condyle may define a sharp corner when transitioning from the first portion to the intermediate portion and transitioning from the intermediate portion to the second portion. The inner edge of the lateral condyle may define a rounded curve when transitioning from the first portion to the intermediate portion and transitioning from the intermediate portion to the second portion. The intermediate portion of the inner edge of the lateral condyle may extend toward the posterior end and toward the outer edge of the lateral condyle along an S-shaped sigmoidal curve. The second portion of the inner edge of the lateral condyle may extend toward the posterior end and the outer edge of the lateral condyle. The intermediate portion of the inner edge of the lateral condyle may extend at an angle oriented farther in the direction of the outer edge of the lateral condyle than an angle in which the second portion extends toward the posterior end and the outer edge of the lateral condyle.

BRIEF DESCRIPTION OF THE DRAWINGS

The features, aspects, and advantages of the present invention will become better understood with regard to the following description, appended claims, and accompanying drawings in which:

DETAILED DESCRIPTION

The present disclosure will now be described more fully hereinafter with reference to the accompanying drawings, in which some, but not all aspects of the disclosure are shown. Indeed, the disclosure may be embodied in many different forms and should not be construed as being limited to the aspects set forth herein. Like numbers refer to like elements throughout.

As used herein, the term "medial," when used in connection with a component or a patient's anatomy, refers to a side or region facing the center of the patient. The term "lateral," when used in connection with a component or a patient's anatomy, refers to a side or region facing toward the patient's side, i.e., away from the center of the patient. The term "anterior," when used in connection with a component or a patient's anatomy, refers to a side or region facing the front of the patient. The term "posterior," when used in connection with a component or a patient's anatomy, refers to a side or region facing the rear of the patient. As used herein, the terms "substantially," "generally," "approximately," and "about" are intended to mean that slight deviations from absolute are included within the scope of the term so modified.

Figure 1A:
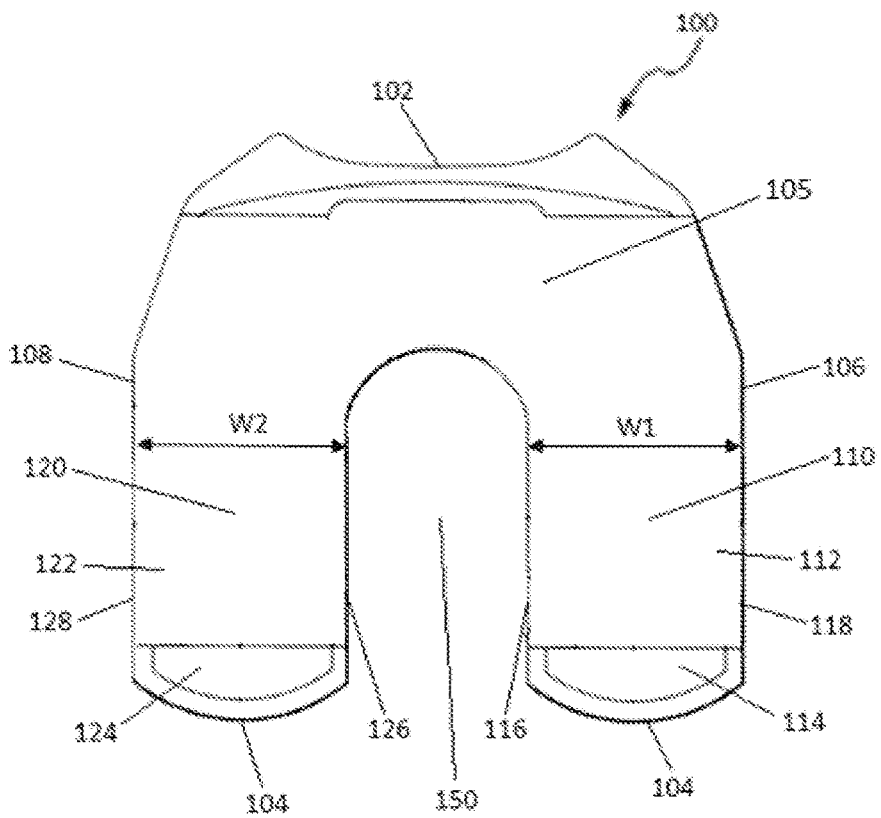
FIGS. 1A-B are top and rear views, respectively, of a femoral component according to an embodiment of the prior art.
Figure 1B:
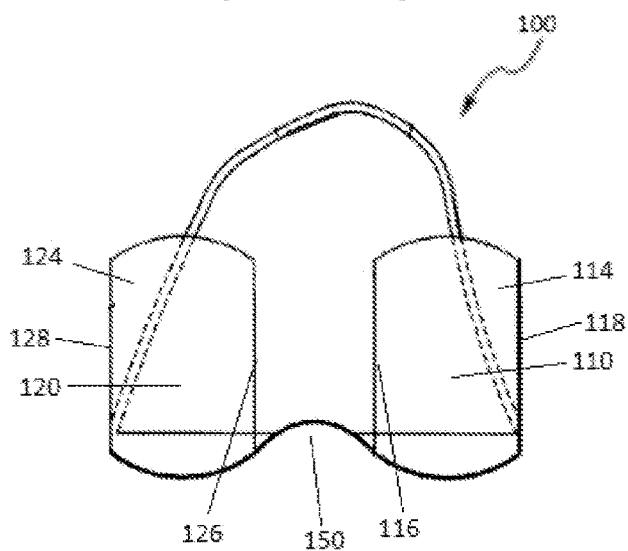

FIGS. 1A-B illustrate a femoral component or implant 100 according to an embodiment of the prior art. Femoral component 100 extends from an anterior end 102 to a posterior end 104 defining a length of the femoral component. Femoral component 100 further extends from a medial edge 106 to a lateral edge 108 defining a width of the femoral component. Femoral component 100 includes an anterior flange 105 which extends along the width of femoral component 100 and defines and an anterior and superior terminal end of the implant. Femoral component 100 also includes a medial condyle 110 that extends from flange 105 on a medial side of femoral component 100. More specifically, medial condyle 110, has a central portion 112 that extends from flange 105 generally in a posterior direction from anterior flange 105, and a posterior portion 114 which extends from central portion 112 generally in a posterior and superior direction, as best shown in FIG. 1B. Femoral component 100 further includes a lateral condyle 120 that extends from flange 105 on a lateral side of femoral component 100. Lateral condyle 120 has a central portion 122 that extends from flange 105 generally in a posterior direction, and a posterior portion 124 extending from central portion 122 generally in a posterior and superior direction, as best shown in FIG. 1B. It is noted that the posterior portions 114 and 124 of the medial and lateral condyles 110, 120 respectively define posterior and superior terminal ends of component 100 opposite that of anterior flange 105.

Medial condyle 110 and lateral condyle 120 define an intercondylar notch 150 therebetween. Anterior flange 105 extends from anterior end 102 to the anterior-most point of intercondylar notch 150. Medial and lateral condyles 110, 120 begin extending from anterior flange 105 at the length of femoral component 100 where intercondylar notch 150 begins. That is, anterior flange 105 ends and condyles 110, 120 begin along an axis extending across the width of femoral component 100 tangential to the anterior-most point of intercondylar notch 150. Medial condyle 110 includes an inner edge 116 adjacent to and partially defining intercondylar notch 150, and an outer edge 118 extending along medial edge 106 of femoral component 100. The distance between inner edge 116 and outer edge 118 defines a medial condylar width W1. Lateral condyle 120 includes an inner edge 126 adjacent to and partially defining intercondylar notch 150, and an outer edge 128 extending along lateral edge 108 of femoral component 100. The distance between inner edge 126 and outer edge 128 defines a lateral condylar width W2. It should be noted that both the medial condylar width W1 and the lateral condylar width W2 remain constant for substantially the entire length of the medial and lateral condyles 110, 120 as they extend from flange 105 to their respective terminal ends. The condyles 110, 120 are about equal in size, and the femoral component 100 is therefore substantially symmetric. Thus, the intercondylar notch 150 formed between the condyles 110, 120 is also substantially symmetric. As described above, a resected femur may not be symmetric, e.g., the lateral condyle may be smaller than the medial condyle. Implanting a symmetric femoral component on such an asymmetric femur may result in overhang of the femoral posterolateral condyle. An improperly fitting prosthesis may cause irritation in a patient as described above.

Figure 2A:
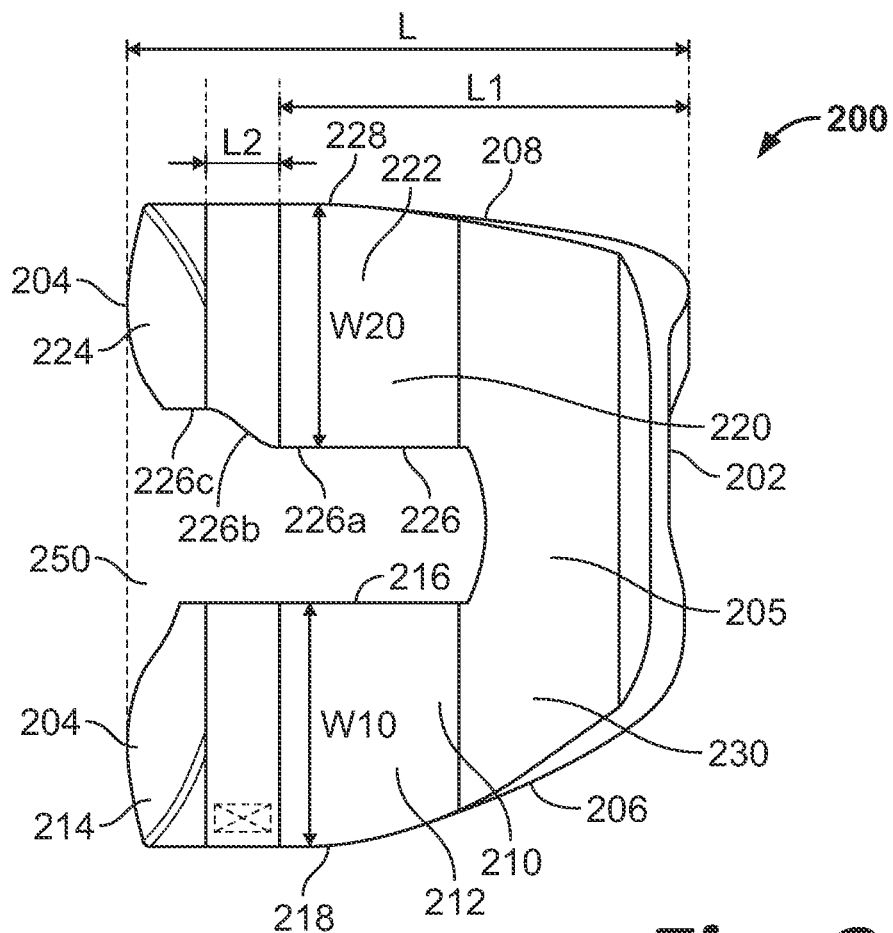
FIGS. 2A-E are top, rear, side, perspective and cross-sectional views, respectively, of a femoral component according to an embodiment of the disclosure.
Figure 2B:
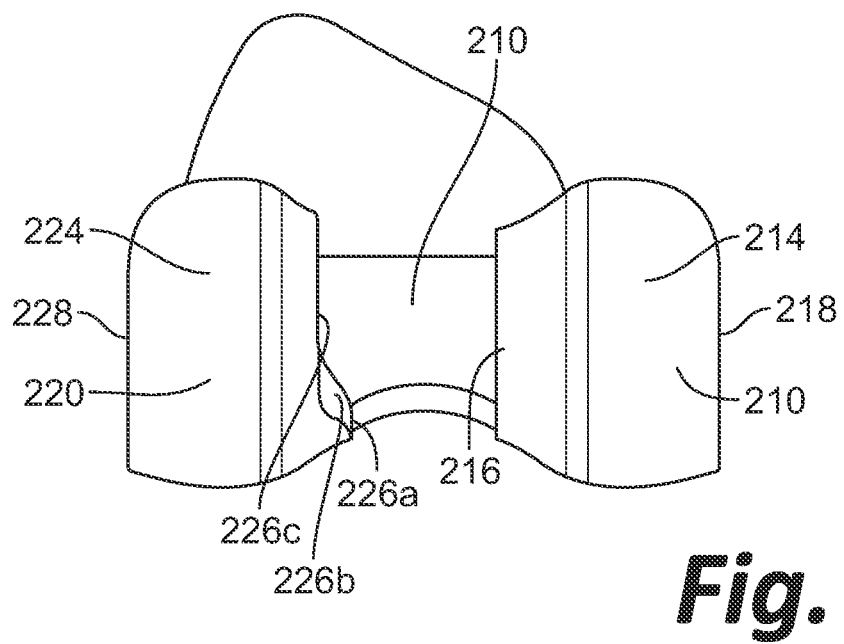

FIGS. 2A-D illustrate a femoral component 200 according to an embodiment of the disclosure. Femoral component 200 extends from an anterior end 202 to a posterior end 204 defining a length L of the femoral component. Femoral component 200 further extends from a medial edge 206 to a lateral edge 208 defining a width of the femoral component. Femoral component 200 includes an anterior flange 205 extending along the width of femoral component 200 and defines anterior end 202. Femoral component 200 includes a medial condyle 210 extending posteriorly from flange 205 on a medial side of femoral component 200. Medial condyle 210 has a central portion 212 that extends from flange 205 generally in a posterior direction, as shown in FIG. 2A, and a posterior portion 214 that extends from central portion 212 generally in a posterior and superior direction, as shown in FIGS. 2A and 2B. Femoral component 200 further includes a lateral condyle 220 that extends from flange 205 on a lateral side. Lateral condyle 220 has a central portion 222 that extends from flange 205 generally in a posterior direction as shown in FIG. 2A, and a posterior portion 224 that extends from central portion 222 generally in a posterior and superior direction, as shown in FIGS. 2A and 2B.

Medial condyle 210 and lateral condyle 220 define an intercondylar notch 250 therebetween. Intercondylar notch 250 may have an arc-shaped anterior extent defined by flange 205. Anterior flange 205 extends from anterior end 202 to the anterior extent of intercondylar notch 250. Medial and lateral condyles 210, 220 begin extending from anterior flange 205 at the length of femoral component 200 where intercondylar notch 250 begins. That is, anterior flange 205 ends and condyles 210, 220 begin along an axis extending across the width of femoral component 200 tangential to the anterior-most point of intercondylar notch 250. Medial condyle 210 includes an inner edge 216 adjacent intercondylar notch 250, and an outer edge 218 extending along medial edge 206 of femoral component 200. Inner edge 216 may lie substantially along a single plane from flange 205 to posterior end 204. The distance between inner edge 216 and outer edge 218 defines a medial condylar width W10. Lateral condyle 220 includes an inner edge 226 adjacent intercondylar notch 250, and an outer edge 228 extending along lateral edge 208 of femoral component 200. The distance between inner edge 226 and outer edge 228 defines a lateral condylar width W20. The distance between inner edge 216 of medial condyle 210 and inner edge 226 of lateral condyle 220 defines an intercondylar notch width. It should be noted that outer edge 218 of medial condyle 210 curves or tapers so that the medial condylar width W10 increases as medial condyle 210 extends from flange 205 until width W10 reaches a maximum value and then remains constant for substantially the remaining length of the medial condyle 210 to its posterior end 204. Thus, medial condyle 210 has a generally constant mediolateral width extending over central portion 212 and posterior portion 214. Lateral condylar width W20 similarly increases as lateral condyle 220 extends from flange 205 until width W20 reaches a maximum value. However, unlike medial condyle 210, width W20 tapers as lateral condyle 220 continues extending toward and approaching posterior end 204. Thus, lateral condylar width W20 becomes narrower as lateral condyle 220 extends posteriorly, whereas medial condylar width W10 remains relatively constant over the same span in the posterior direction. Additionally, the intercondylar width increases as lateral condylar width W20 decreases. As shown in FIG. 2A, this increase in width of the intercondylar space and corresponding decrease in condylar width W20 of lateral condyle 220 is due to the tapering of inner edge 226.

It should be noted that inner edge 226 may extend in a superior direction as shown in FIG. 2B, however, the following description is described according to a top view of femoral component 200 as shown in FIG. 2A for ease of illustration. Inner edge 226 of lateral condyle 220 includes a first portion 226a extending from flange 205 in a posterior direction. First portion 226a may lie in a first plane. Inner edge 226 further includes an intermediate portion 226b extending linearly at an angle oblique to the first portion 226a in the posterolateral direction (i.e., toward both posterior end 204 and lateral edge 208 of femoral component 200/outer edge 228 of condyle 220). The inner edge 226 further includes a second portion 226c extending from the intermediate portion 226b to posterior end 204 in a straight line parallel to the first portion 226a. Second portion 226c may lie in a second plane parallel to and offset from the first plane. Lateral condylar width W20 decreases as lateral condyle 226 extends in the posterior direction along intermediate portion 226b. Thus, lateral condylar width W20 may be smaller where lateral condyle 226 extends along intermediate and second portions 226b, 226c relative to where lateral condyle 226 extends along first portion 226a. It is contemplated that lateral condylar width W20 may be up to 20% smaller than medial condylar width W10 when measured at the same length L. In other words, lateral condylar width W20 may be up to 20% smaller than the medial condylar width W10 within a plane which may extend in the medial-lateral direction through both medial and lateral condyles 210, 220, e.g., through the intermediate or second portions 226b, 226c of the lateral condyle 220. Intercondylar notch 250 is therefore asymmetric. As illustrated in FIG. 2A, inner edge 226 has rounded or radiused edges where inner edge 226 transitions from first portion 226a to intermediate portion 226b and from intermediate portion 226b to second portion 226c. As described above, a resected femur may not be symmetric, e.g., the lateral condyle may be smaller than the medial condyle. The tapering width of the lateral condyle 220 may provide for an improved fit of the femoral component 200 on a resected femur. An improved fit may prevent or relieve a patient from ailments or symptoms associated with a poorly fitting prosthesis as described above.

Implant 200 may be prepared as a patient-specific implant. In preparing such an implant, the patient's anatomy at the distal femur may be scanned, such as by a CT scan or other use of x-rays or by magnetic resonance imaging (MRI) or other known imaging device. The scanned image may then be converted to virtual patient-specific bone image on a monitor or other display using computer-aided modeling and segmentation software. Such software may be but is not limited to Imorphics™, which is wholly owned by Imorphics Limited, a subsidiary of Stryker® Corporation, Stryker® Orthopaedics Modeling and Analytics (SOMA) by Stryker® Corporation, GeoMagic® by 3D Systems, Inc., and 3D Slicer software developed by the Massachusetts Institute of Technology. A manual segmentation or an automatic segmentation process, such as either of the processes described in U.S. Pat. No. 7,584,080 and U.S. Patent Application Publication No. 2011/0194739 A1, which are hereby incorporated by reference in their entireties herein, may be used. A virtual implant may be implanted onto the virtual bone and the widths W10 and W20 may be adjusted to the specific patient's anatomy.

Alternatively, implant 200 may be semi-custom in which a database of bones, such as Stryker's SOMA database, may be used to analyze bone data within defined patient populations to determine appropriate widths W20 and W10 for each of such populations. A series or kit of implants may be fabricated with each defined population in mind. An appropriate implant 200 may be selected for the specific patient depending on the population to which that patient belongs.

As illustrated in FIG. 2A, femoral component 200 has as a length L defined by the distance between anterior end 202 and posterior end 204. Femoral component 200 further has a length L1 defined by the distance between anterior end 202 and the posterior-most point of the first portion 226a of the inner edge 226 of the lateral condyle 220. In other words, length L1 extends from the anterior end 202 to a line extending in the medial-lateral direction where the first portion 226a transitions to the intermediate portion 226b. Femoral component 200 further has a length L2 defined by the length of the intermediate portion 226b of the inner edge 226 of the lateral condyle 220. That is, L2 is the distance between the line extending in the medial-lateral direction where the first portion 226a transitions to the intermediate portion 226b, and a line extending in the medial-lateral direction where the intermediate portion 226b transitions to the second portion 226c. It is contemplated that length L1 may have a value that is between approximately 70% and 75% of the value of length L. It is also contemplated that length L2 may have a value that is between approximately 10% and 15% of the value of length L. It should be noted that alternate embodiments of the femoral component may have a length L1 that is between approximately 65% and 80% of length L, and a length L2 that is between approximately 5% and 20% of length L. Such values may be determined through a bone database analysis, such as the SOMA database mentioned above.

Figure 2C:
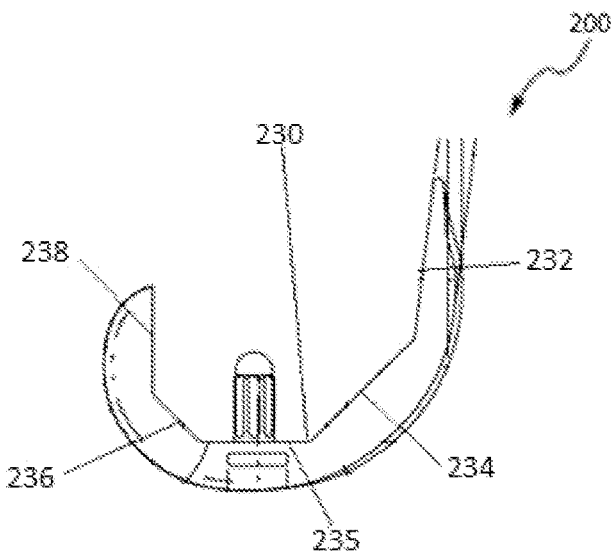

Femoral component 200 has a superior surface 230 (i.e., the surface of the femoral component 200 shown in FIG. 2A) that is configured to contact bone, the superior surface 230 includes a plurality of planar bone-contacting surfaces. As shown in FIG. 2C, superior surface 230 includes anterior surface 232 extending generally in a superior-inferior direction, anterior chamfer surface 234 extending at an oblique angle to anterior surface 232, distal surface 235 extending generally orthogonal to anterior surface 232, posterior chamfer surface 236 extending at an oblique angle to distal surface 235, and posterior surface 238 extending generally in a superior-inferior direction. Thus, anterior chamfer surface 234 is disposed between anterior surface 232 and distal surface 235, and posterior chamfer surface 236 is disposed between posterior surface 238 and distal surface 235. FIG. 2E illustrates a cross-sectional view of femoral component 200 along axis E (shown in FIG. 2D), the cross-section taken along the width of the femoral component 200 at the intersection between distal surface 235 and posterior chamfer surface 236 in a plane parallel to posterior surface 238, FIG. 2E illustrating a view in a posterior direction from axis E.

Figure 2D:
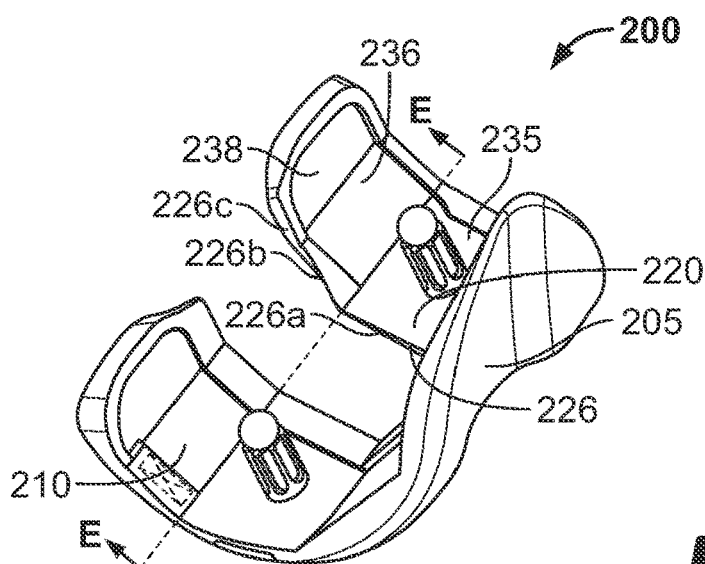
Figure 2E:
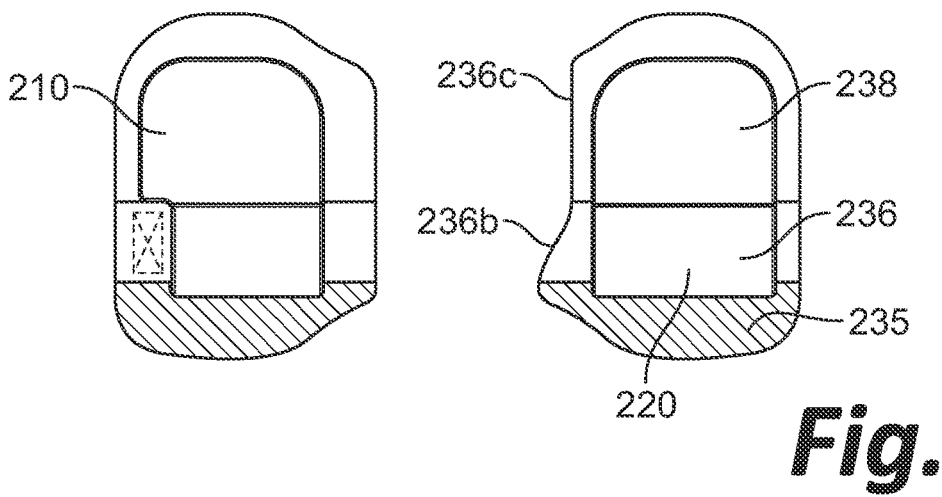

As shown in FIGS. 2D-E, intermediate portion 226b of inner edge 226 of lateral condyle 220 is intersected by posterior chamfer surface 236. In other words, intermediate portion 226b of inner edge 226 is located on a portion of lateral condyle 220 corresponding to a runout location of posterior chamfer surface 236 on lateral condyle 220. It should be noted that intermediate portion 226b may not extend beyond posterior chamfer surface 236 in an anterior nor posterior direction. In other words, length L2 (i.e., the length of intermediate portion 226b in the anteroposterior direction) shown in FIG. 2A may be equal to or less than a length defined by the distance in which posterior chamfer surface 236 extends in an anteroposterior direction. Such lengths are to be understood as taken in an anteroposterior direction only and do not include length components in a superior-inferior direction.

Figure 3:
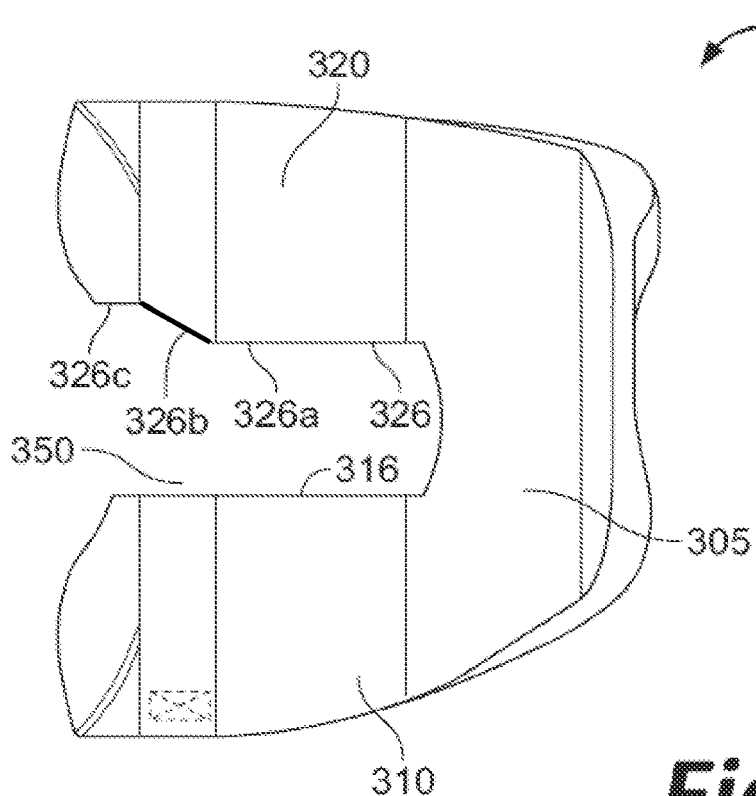
FIG. 3 is a top view of a femoral component according to another embodiment of the disclosure.

FIG. 3 illustrates a femoral component 300 according to another embodiment of the disclosure. Femoral component 300 is substantially similar to femoral component 200 described above. Femoral component 300 includes medial condyle 310 and lateral condyle 320 extending from flange 305. Medial condyle 310 has an inner edge 316 which extends in the posterior and superior directions generally corresponding to the direction of medial condyle 310. Lateral condyle 320 has an inner edge 326 adjacent intercondylar notch 350. It should be noted that inner edge 326 may extend in a superior direction, however, the following description is described according to a top view of femoral component 300 as shown in FIG. 3 for ease of illustration. Inner edge 326 includes a first portion 326a extending in a posterior direction from flange 305. Inner edge 326 further includes an intermediate portion 326b extending linearly at an oblique angle to the first portion 326a in the posterolateral direction. Inner edge 326 further includes a second portion 326c extending from the intermediate portion 326b in the posterior direction parallel to the first portion 326a. As illustrated in FIG. 3, inner edge 326 has sharp edges where inner edge 326 transitions from first portion 326a to intermediate portion 326b and from intermediate portion 326b to second portion 326c.

Figure 4:
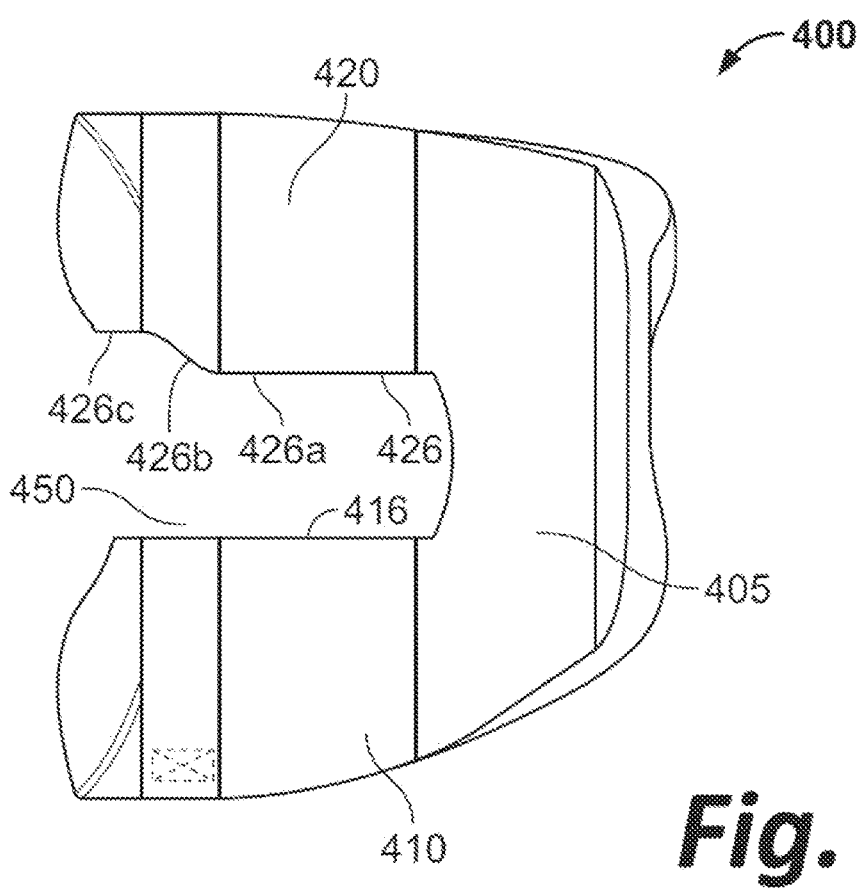
FIG. 4 is top view of a femoral component according to another embodiment of the disclosure.

FIG. 4 illustrates a femoral component 400 according to another embodiment of the disclosure. Femoral component 400 is substantially similar to femoral component 200 described above. Femoral component 400 includes medial condyle 410 and lateral condyle 420 extending from flange 405. Medial condyle 410 has an inner edge 416 which extends in the posterior and superior directions generally corresponding to the direction of medial condyle 410. Lateral condyle 420 has an inner edge 426 adjacent intercondylar notch 450. It should be noted that inner edge 426 may extend in a superior direction, however, the following description is described according to a top view of femoral component 400 as shown in FIG. 4 for ease of illustration. Inner edge 426 includes a first portion 426a extending in a posterior direction from flange 405. Inner edge 426 further includes an intermediate portion 426b extending in an S-shaped sigmoidal curve in the posterolateral direction. Inner edge 426 further includes a second portion 426c extending from the intermediate portion 426b, the second portion 426c extending in the posterior direction parallel to the first portion 426a. As illustrated in FIG. 4, inner edge 426 has rounded edges where inner edge 426 transitions from first portion 426a to intermediate portion 426b and from intermediate portion 426b to second portion 426c.

Figure 5:
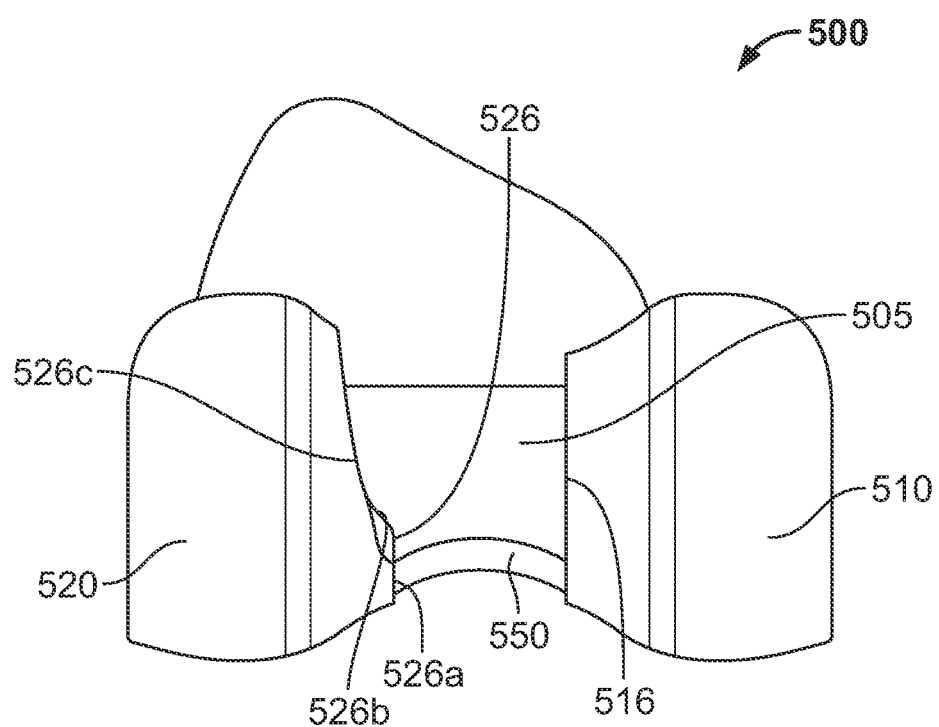
FIG. 5 is a rear view of a femoral component according to another embodiment of the disclosure.

FIG. 5 illustrates a femoral component 500 according to another embodiment of the disclosure. Femoral component 500 is substantially similar to femoral component 200 described above. Femoral component 500 includes medial condyle 510 and lateral condyle 520 extending from flange 505. Medial condyle 510 has an inner edge 516 which extends in the posterior and superior directions generally corresponding to the direction of medial condyle 510. Lateral condyle 520 has an inner edge 526 adjacent intercondylar notch 550. Inner edge 526 includes a first portion 526a extending in a posterior direction from flange 505 as the corresponding portion of the lateral condyle extends in the posterior direction. Inner edge 526 further includes an intermediate portion 526b extending in a posterolateral direction as the corresponding portion of the lateral condyle 520 extends in the posterior and superior directions, creating a taper in the width of lateral condyle 520. Lateral condyle 520 further includes a second portion 526c further extending in the posterolateral direction as the corresponding portion of the lateral condyle 526 extends in the posterior and superior directions, thus further tapering the width of lateral condyle 520. The rate of taper may be greater along the intermediate portion 526b than the second portion 526c. That is, the intermediate portion 526b may extend at an angle farther in the lateral direction than the second portion 526c.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A femoral component for a knee prosthesis, comprising:
   an anterior flange;
   a medial condyle extending from the anterior flange to a posterior end thereof and having inner and outer edges defining a medial condyle width therebetween, the inner edge lying substantially along a single plane from the anterior flange to the posterior end of the medial condyle; and
   a lateral condyle extending from the anterior flange to a posterior end thereof and having inner and outer edges defining a lateral condyle width therebetween, the inner edge of the lateral condyle having a first portion, a second portion, and an intermediate portion,
   wherein the inner edges of the lateral and medial condyles define an intercondylar notch and lateral and medial extents of the intercondylar notch such that an intercondylar width extends between the inner edges of the lateral and medial condyles,
   wherein the inner edge of the lateral condyle tapers toward the outer edge of the lateral condyle at the intermediate portion such that the intercondylar width is greater along the second portion of the inner edge of the lateral condyle than along the first portion of the lateral condyle, and
   wherein the intermediate portion of the inner edge of the lateral condyle begins at 70-75% of an anteroposterior length of the femoral component from an anterior extent of the femoral component.

2. The femoral component of claim 1, wherein the femoral component includes a bone contacting side having a plurality of planar bone contacting surfaces comprised of an anterior surface, a distal surface, a posterior surface, an anterior chamfer surface, and a posterior chamfer surface, the anterior chamfer surface being disposed between the anterior surface and distal surface, the posterior chamfer surface being disposed between the distal surface and posterior surface.

3. The femoral component of claim 2, wherein the intermediate portion of the inner edge of the lateral condyle is intersected by the posterior chamfer surface.

4. The femoral component of claim 2, wherein the intermediate portion has a length extending in an anteroposterior direction that is no longer than a length of the posterior chamfer surface.

5. The femoral component of claim 1, wherein the intermediate portion has an anteroposterior length of 10% to 15% the full anteroposterior length of the femoral component.

6. The femoral component of claim 1, wherein the first portion of the inner edge lies in a first plane and the second portion of the inner edge lies in a second plane.

7. The femoral component of claim 6, wherein the second plane is offset and parallel to the first plane.

8. The femoral component of claim 1, wherein the second portion extends from the intermediate portion to the posterior end of the lateral condyle.

9. The femoral component of claim 1, wherein the intercondylar width is constant along the first portion of the inner edge of the lateral condyle.

10. The femoral component of claim 1, wherein the anterior flange defines an anterior extent of the intercondylar notch, the anterior extent of the intercondylar notch being arc shaped.

11. The femoral component of claim 1, wherein the lateral condyle width tapers from wider to narrower in a posterior direction along the inner edge of the intermediate portion such that the lateral condyle width is narrower at the second portion of the inner edge than at the first portion of the inner edge.

12. The femoral component of claim 1, wherein the intercondylar notch is asymmetric.

13. The femoral component of claim 1, wherein the lateral condyle width along a length of the second portion is up to 20% less than the medial condyle width at the same anteroposterior length of the medial condyle.

14. The femoral component of claim 1, wherein the intermediate portion of the inner edge of the lateral condyle extends linearly toward the posterior end of the femoral component and the outer edge of the lateral condyle.

15. The femoral component of claim 14, wherein the inner edge of the lateral condyle defines a sharp corner when transitioning from the first portion to the intermediate portion and transitioning from the intermediate portion to the second portion.

16. The femoral component of claim 14, wherein the inner edge of the lateral condyle defines a rounded curve when transitioning from the first portion to the intermediate portion and transitioning from the intermediate portion to the second portion.

17. The femoral component of claim 1, wherein the intermediate portion of the inner edge of the lateral condyle extends toward the posterior end and toward the outer edge of the lateral condyle along an S-shaped sigmoidal curve.

18. The femoral component of claim 1, wherein the second portion of the inner edge of the lateral condyle extends toward the posterior end and the outer edge of the lateral condyle.

19. The femoral component of claim 18, wherein the intermediate portion of the inner edge of the lateral condyle extends at an angle oriented farther in the direction of the outer edge of the lateral condyle than an angle in which the second portion extends toward the posterior end and the outer edge of the lateral condyle.

20. A femoral component for a knee prosthesis, comprising:
   an anterior flange;
   a medial condyle extending from the anterior flange to a posterior end thereof and having inner and outer edges defining a medial condyle width therebetween, the inner edge lying substantially along a single plane from the anterior flange to the posterior end of the medial condyle; and
   a lateral condyle extending from the anterior flange to a posterior end thereof and having inner and outer edges defining a lateral condyle width therebetween, the inner edge of the lateral condyle having a first portion, a second portion, and an intermediate portion,
   wherein the inner edges of the lateral and medial condyles define an intercondylar notch and lateral and medial extents of the intercondylar notch such that an intercondylar width extends between the inner edges of the lateral and medial condyles,
   wherein the inner edge of the lateral condyle tapers toward the outer edge of the lateral condyle at the intermediate portion such that the intercondylar width is greater along the second portion of the inner edge of the lateral condyle than along the first portion of the lateral condyle,
   wherein the femoral component includes a bone contacting side having a plurality of planar bone contacting surfaces comprised of an anterior surface, a distal surface, a posterior surface, an anterior chamfer surface, and a posterior chamfer surface, the anterior chamfer surface being disposed between the anterior surface and distal surface, the posterior chamfer surface being disposed between the distal surface and posterior surface, and wherein the intermediate portion of the inner edge of the lateral condyle is intersected by the posterior chamfer surface.

* * * * *